United States Patent [19]

Randolph

[11] 4,015,628
[45] Apr. 5, 1977

[54] DILUTION DEVICE

[76] Inventor: Ellwood A. Randolph, 680 Sharp Lane, Baton Rouge, La. 70815

[22] Filed: Dec. 12, 1975

[21] Appl. No.: 640,203

[52] U.S. Cl. ............................... 137/566; 137/571
[51] Int. Cl.$^2$ ............................................. B01F 3/08
[58] Field of Search .......... 137/571, 575, 566, 597; 210/252, 255, 258

[56] References Cited

UNITED STATES PATENTS

| | | | |
|---|---|---|---|
| 526,695 | 10/1894 | Emery | 210/252 |
| 2,827,172 | 3/1958 | Frazier | 210/252 X |
| 3,350,298 | 10/1967 | Carr | 210/252 X |
| 3,849,197 | 11/1974 | Sorrentino | 137/571 X |

*Primary Examiner*—William R. Cline
*Attorney, Agent, or Firm*—Llewellyn A. Proctor

[57] ABSTRACT

Apparatus for the staged, controlled dilution of a sample comprised of a particulate solids containing fluid with a preselected amount of a fluid diluent. The apparatus consists of a plurality of vessels connected together in series such that diluent introduced into the first vessel flows consecutively from vessel to vessel, to exit from the last vessel of the series. The raw sample of particulate solids is introduced into the last vessel of the series, diluted, and progressively diluted specimens of the original sample are transferred from vessel to vessel countercurrent to the flow of diluent. The sample, diluted with a preselected quantity of diluent in the several stages of dilution, is finally removed from the first vessel of the series, suitable for analysis, e.g., via the use of electronic counters. Preferably from about 3 to about 5 dilution stages are provided, and positive displacement pumps are used to withdraw diluted sample from a downstream stage and reintroduce the sample into an upstream stage to further progressively dilute the sample. Preferably, also, the pumps are driven by a common drive means to assure better control of flow rates.

9 Claims, 3 Drawing Figures

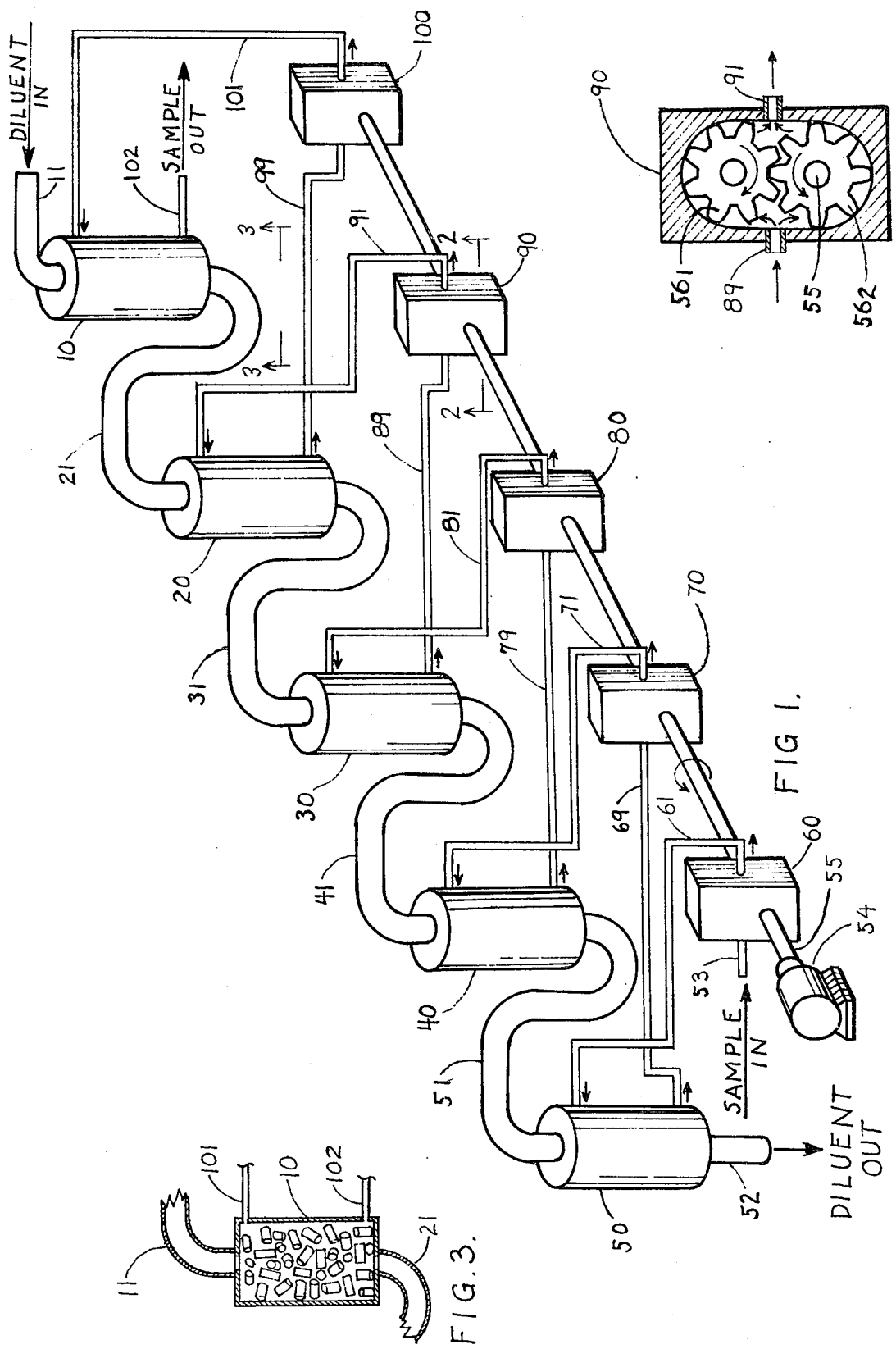

DILUTION DEVICE

Solids and semi-solids are often produced and handled, e.g., in industrial processes, as suspensions contained within a fluid, e.g., a gas or liquid. Particulate solids are thus often conveyed through processes, or discharged therefrom as components of high velocity gas streams or as liquid slurries, or thick muds. One reason for the handling of solids in this manner is that it is more economical to move fluids than solids and hence, in the process industries, solids are transported as fluids whenever possible. Also, in some process industries, the solids are formed in situ as by-products of chemical or bacteriological reactions and it is more convenient to transport the solids through the process as a fluid medium.

In the process industries it is often essential to control the particle size and particle size distribution of the suspended solids and, to accomplish this, it is generally necessary to monitor and analyze process streams. Samples of fluid specimen are thus often withdrawn from a process at critical control points, or locations and analyzed. If the solids content of a fluid specimen is not too highly concentrated, a direct count can be made of the particles of given size, or sizes, contained with a specific volume of fluid. Electronic counters are thus commercially available wherein the solids particles of a flowing stream can be directly and routinely counted both as regards specific particle sizes, and specific particle size distributions.

Often as not, however, the concentration of particulate solids within a process stream is too great, and outside the range of concentration of particulate solids which can be analyzed or directly counted by available electronic counters within a given time frame. The instrument is simply unable to "see" and count individual particles because of the close proximity of the solids particles to one another. Dilution of the fluid specimen by the addition of accurately measured volumes of a diluent effectively separates the particles so that they can be counted, after which time the particulate solids of the original specimen can be calculated. This technique is often used in control laboratories.

Electronic counters for use in analyzing particulate solids containing process streams have gained wide acceptance by industry, and by the scientific community, generally, for use in the counting of solids particles of pre-selected size, or sizes, or according to pre-selected particle size distributions. In recent years, tremendous advantages have been offered by the combination of electronic counters and modern data gathering techniques for the monitoring of process streams on a continuous basis. Because these means of analysis greatly reduce operating manpower, without decrease in accuracy or precision, there is considerable demand for means of adapting and extending the capabilities of electronic counters for performing such analyses. One means is by providing a technique or method for the controlled, accurate dilution of fluid particulate solids process streams to pre-selected solids levels, preferably on a continuous basis.

It is, accordingly, a primary object of the present invention to fulfill these needs.

A particular object is to provide new and novel apparatus for the controlled dilution of particulate solids containing fluid specimens, particularly apparatus capable of integration with modern electronic counters for use in performing analyses, which data can be stored, if desired.

A further object is to provide apparatus of simple and relatively inexpensive construction, particularly apparatus which can be readily produced by mass production techniques, readily serviced and operated.

These objects and others are achieved in accordance with the present invention comprised generally of apparatus which includes, in combination (a) a plurality of vessels connected in series such that a diluent can be introduced into the first vessel, and diluent withdrawn from the last vessel, as determined by the direction of flow of the diluent, (b) means for the introduction and dilution of a sample comprising a particulate solids containing fluid into the diluent entry side of the last vessel of the series, (c) means associated with each adjacent pair of the serially connected vessels for withdrawal of a diluted fluid sample from the diluent exit side of a downstream vessel, (d) for reintroduction of the diluted fluid sample into the diluent entry side of the upstream vessel of the associated pair of vessels, and (e) means for withdrawal of a sample of preselected dilution from the diluent exit side of the first vessel of the series.

In its more practical aspects, the apparatus combination is one comprising a plurality, usually from about three to about five, of elongate vessels connected in series such that a diluent can be introduced into the first vessel and withdrawn from the last vessel of the series, while a sample of particulate solids containing fluid is introduced countercurrent to the flow of diluent, in each stage the sample being admixed with a preselected amount of diluent withdrawn from a previous vessel of the series, as determined by the direction of flow of the diluent. The means for the introduction of a particulate solids fluid sample into the last vessel of the series, for the withdrawal of diluted sample from the diluent exit side of a downstream vessel and for its reintroduction into the diluent entry side of an upstream vessel of an associated pair, referred to as steps (b), (c) and (d), supra, is preferably a bank of pumps of the positive displacement type. These portions of the combination thus comprise, preferably, a plurality of positive displacement pumps, each provided with the usual suction and discharge sides, the suction side of a first of the pumps being connected with a sample supply source and the discharge side with the last vessel of the series, each of the other pumps being operatively associated with each adjacent pair of the serially connected vessels; a plurality of sample injection lines equal in number to the number of serially connected vessels, the first connecting the discharge side of the first pump with the diluent entry side of the last vessel of the series, the others connecting the discharge side of the other pumps with the diluent entry side of a vessel upstream of the pair of vessels associated with a pump; a plurality of sample withdrawal lines equal in number to the number of pumps, a first being connected with the suction side of the first pump for supplying a sample of particulate solids containing fluid from a source of supply, while each of the others connect the suction side of a pump with the diluent exit side of a downstream vessel of a pair of vessels in association with a pump; and a dilute sample outlet line located at the diluent exit side of the first vessel of the series. In such apparatus, a sample of a particulate solids containing fluid of relatively high solids concentration can be introduced into the suction side of the first pump of the series, as determined by the direction of flow of the sample, the sample injected into the last vessel of the series, progressively diluted in the series of separate stages, and the diluted sample discharged from the diluent exit side of the first vessel of the series, as determined by the direction of flow of the diluent.

The characteristics of a preferred sample dilution apparatus, and the principle of its operation, will be more fully understood by reference to the following detailed description of preferred embodiments, and to the attached drawings to which reference is made as the description unfolds. Similar numbers are used to represent similar parts or components in the several figures. Subscripts are used where there is a plurality of similar parts, or components.

In the drawings:

FIG. 1 depicts a perspective view of preferred apparatus for the controlled dilution of a particulate solids containing fluid sample, of relatively high solids, with a preselected amount of fluid diluent.

FIG. 2 depicts a view taken through section 2—2 of FIG. 1.

FIG. 3 depicts a view taken through section 3—3 of FIG. 1.

Referring generally to FIG. 1, there is shown a series of five vertically aligned elongate vessels 10,20,30,40,50, connected together such that a fluid diluent introduced into a first vessel of this series passes consecutively through the several vessels and egresses from the last vessel of the series. A bank of pumps 60,70,80,90,100 is provided. The pumps are provided for the purpose of introducing countercurrently a sample comprised of a particulate solids fluid specimen of relatively high solids concentration into the last vessel 50 of the series, as determined by the direction of diluent flow, for the removal of diluted sample from the diluent exit side of each downstream vessel and for reintroduction of the diluted sample into the diluent inlet side of each adjacent upstream vessel of the series for further dilution of the sample, and for removal of the diluted sample from the exit side of the first vessel of the series.

In FIG. 1, specifically, there is thus shown a plurality of five elongated, vertically aligned vessels serially connected one to another such that a diluent introduced via line 11 into the top of vessel 10 flows downwardly therethrough to exit via line 21, is introduced via line 21 into the top of vessel 20, flows downwardly therethrough to exit via line 31, is introduced via line 31 into the top of vessel 30, flows downwardly therethrough to exit via line 41, is introduced via line 41 into the top of vessel 40, flows downwardly therethrough and exits via line 51, and is introduced via line 51 into the top of vessel 50, flows downwardly therethrough and exits via line 52. A raw sample of particulate solids contained within a fluid, generally a liquid, most often water, is introduced countercurrently into the last vessel 50 of the series via line 53 into the suction side of a positive displacement type pump 60. The raw sample in this, the first stage of dilution, is transferred by action of the pump 60 via outlet line 61 at the discharge side of the pump into the upper side, or diluent entry side, of vessel 50. The raw sample on entry into vessel 50, is admixed with diluent which enters via line 51 into the top of vessel 50. The diluted sample, after such mixing, is then discharged from the lower portion or diluent exit side of the vessel 50 via line 69.

The second, third, fourth and fifth stage of dilution of the sample is completed in vessels 40,30,20 and 10, respectively, and the diluted particulate solids specimen is then dicharged from the bottom, or diluent exit side, of vessel 10 constituting the first vessel of the series, as determined by the location wherein the diluent is initially introduced. Thus, the sample from the first stage of dilution is removed from the bottom of vessel 50 via line 69 and transferred via line 71 under the positive action of pump 70 to the upper side of vessel 40; the sample from the second dilution stage is removed from the lower end of vessel 40 via line 79 and transferred via the line 81 under the positive action of pump 80 to the upper side of vessel 30; the sample from the third dilution stage is removed from the lower end of vessel 30 via line 89 and transferred via the line 91 under the positive action of pump 90; the sample from the fourth dilution stage is removed from the lower end of vessel 20 via line 99 and transferred via line 101 under the positive action of pump 100 to the upper side of vessel 10, the first vessel of the series. Within vessel 10 the fifth, and final, stage of dilution, dilution of the sample is completed, and the diluted sample is discharged from the lower side of vessel 10 via line 102 and, suitably, is passed to an electronic counter or other type of analytical instrument (not shown) for exact measurement of particulate solids.

In dilution of a raw sample, the amount of dilution is controlled primarily by the number and fluid capacity of the vessels 10,20,30,40,50 and by the flow rates between said vessels. Adequate mixing of the sample with the diluent can be achieved by various means, and is preferably achieved within each of the several vessels by various known types of packing added in controlled quantities to vessels of preselected size to provide known volumes. Granular types of packing, constituted of material inert or unreactive with the fluids passed therethrough, and large enough to avoid excessive pressure drops, are generally satisfactory, e.g., spheres, rings, cylindrical shapes, tubes and the like. A preferred method of controlling flow rates between the several stages of dilution (i.e., between dilution stages 1 and 2; between dilution stages 2 and 3; between dilution stages 3 and 4; and between dilution stages 4 and 5) is to employ a common drive means to operate these several pumps. This is shown by reference to FIG. 1 wherein all of pumps 70,80,90,100 are driven by the motor 54 operatively connected therewith via a shaft 55. Suitably, also, as shown in the figure, the motor 54 also drives pump 60, via connection through shaft 55, which is used to introduce the raw undiluted sample into vessel 50, the last vessel of the series.

The term "pump" as used herein means, e.g., pumps, fans, blowers, compressors, and the like, which can be used to impart the required energy to the fluid to effect its transport, or movement, through the vessels and conduits. Positive displacement of the fluid is necessary to assure accuracy. In a positive displacement pump, as defined herein, a discrete quantity of fluid is trapped in a chamber, which is alternately or continuously filled and emptied through the discharge. Piston, plunger, rotary and gear pumps, particularly the latter, prove admirably suitable.

A preferred gear pump, as depicted by reference to FIGS. 1 and 2, particularly the latter, is one wherein two impellers $56_1, 56_2$ are contained within a casing 90, the impellers 56 taking the form of toothed-gear wheels, helical gears, or lobed cams. In any case, the impellers $56_1, 56_2$ rotate with extremely small clearance between each other and between the surface of an impeller and the casing 90. The two impellers 56 rotate in the direction shown by the arc-shaped arrows, the upper impeller $56_1$ being driven by the lower impeller $56_2$ which is adjoined to drive shaft 55. The suction side is to the left side of FIG. 2, to which fluid is admitted via line 89. As the space between the teeth of the impellers 56 pass the suction side, fluid is impounded between them, forced circumferentially around the inside of the casing 90 to the discharge side to the right side of FIG. 2, and forced out through the outlet line 91. The straight arrows indicate the direction of flow, i.e., into the pump via line 89 and out of the pump via line 91.

The following example, simulated in part, is illustrative of the efficacy of the present invention.

EXAMPLE

A series of five tubular vessels were connected together in series as depicted by reference to FIGS. 1 through 3. Each of the vessels were thus connected together via a diluent supply line which entered into the top of a vessel and exited via the bottom thereof, the exit line in each instance constituting a diluent entry line into the top of a subsequent vessel of the series. A bank of five gear type pumps were employed, the suction side of the first pump of the series being connected to a line from a sample supply source, the discharge side of said first pump being connected via a line to the diluent entry side of the last vessel of the series, as determined by the direction of flow of the diluent. The suction side of each of the other pumps, respectively, was connected via a line from the diluent exit side of a vessel, while its discharge side was connected via a line to the diluent entry side of an adjacent upstream vessel, as determined by the direction of diluent flow. All of the pumps were interconnected one to another via a common shaft, and driven by a common motor, as depicted in the figures. Diluted specimen was removed from the diluent exit side of the first vessel of the series.

Water was continuously introduced as a diluent at the rate of 1600 cc/min into the first vessel of the series and, of course, discharged from the last vessel of the series at the same rate. A specimen, comprised of a slurry of particulate solids particles in water, was continuously introduced into the last vessel (stage 1) of the series. The slurry specimen was introduced and passed from one vessel into another at a rate of 100 cc/min, the rate of slurry addition having been controlled by a constant pump shaft speed. Thus, the dilution ratio for each stage was set at 16:1.

The slurry specimen introduced into the first stage contained approximately one million solids particles per 100 cc of sample, the specimen having been diluted within each stage essentially as follows:

| Stage No. | Dilution Ratio | Solids Particles, ppm |
| --- | --- | --- |
| 1 | 0.0625000 | 62,500 |
| 2 | 0.0039063 | 3,906 |
| 3 | 0.0002441 | 244 |
| 4 | 0.0000152 | 15 |
| 5 | 0.0000009 | 1 |

It is apparent that various modifications and changes can be made in the apparatus without departing the spirit and scope of the present invention. The number of vessels and their orientation is optional. The type of pump used is of the positive displacement type, but considerable latitude in the selection of pumps is feasible. The apparatus is constructed of materials substantially inert or nonreactive to the chemical or corrosive action of the diluent to be used, and the raw particulate solids containing fluid specimens to be diluted and dispensed. The vessels and lines of the apparatus are normally constructed of metal, but can be constructed of glass or a plastic or plastic-like material. The lines, or conduits, used in the apparatus are normally constructed of metal, but can be constructed of plastic, e.g., ferrous metals such as iron, iron alloys, steel, stainless steels, and the like; or such metals as aluminum, nickel, magnesium, brass, copper, bronze, chrome, alloys of these and other metals, and the like. The pumps are normally constructed of various metals.

The packing used within the vessels is normally formed of rigid or semi-rigid, resilient form of plastic or plastic-like materials. The plastics can be applied as a laminate or protective film.

It is apparent that various changes, such as in the absolute or relative dimensions of the parts, materials used, and the like, as well as the suggested mode of withdrawing or delivering fluids, can be made without departing the spirit and scope of the invention, as will be apparent to those skilled in this art.

Having described the invention, what is claimed is:

1. In combination, apparatus for the controlled dilution with a preselected amount of fluid diluent, of a sample comprised of a particulate solids containing fluid comprising a plurality of vessels serially connected one to another, wherein the total of a diluent stream can be introduced into a first vessel to flow from one preceding vessel to the next of the series, the total diluent passing from the diluent entry side of a vessel and egressing from the diluent exit side of said vessel, and egressing finally from the diluent exit side of the last vessel of the series, as determined by the direction of flow of the diluent, means for the introduction of a sample comprising a particulate solids containing fluid into the diluent entry side of the last vessel of the series, the particulate solids containing fluid and diluent being thoroughly admixed one with the other to form a homogeneous mixture, means associated with each adjacent pair of the serially connected vessels for withdrawal of the total of the fluid effluent from the diluent exit side of a downstream vessel, and for reintroduction of the total of the fluid effluent (fluid) into the diluent entry side of the upstream vessel of the associated pair of vessels, the particulate solids containing fluid and diluent being thoroughly admixed one with the other in each of the vessels to form a homogeneous mixture, and means for withdrawal of a diluted sample from the diluent exit side of the first vessel of the series, whereby a sample of a particulate solids containing fluid of relatively high solids concentration can be introduced into the last vessel of the series, and the diluted sample discharged from the first vessel of the series.

2. In combination, apparatus for the controlled dilution, with a preselected amount of fluid diluent, of a sample comprised of a particulate solids containing fluid comprising a plurality of vessels serially connected one to another, wherein the diluent can be introduced into the first vessel to flow from one preceding vessel to the next of the series, the diluent passing from the diluent entry side of a vessel and egressing from the diluent exit side of said vessel, and egressing finally from the diluent exit side of the last vessel of the series, as determined by the direction of flow of the diluent, a plurality of pumps for transport of said particulate solids containing fluid sample, a first in operative association with a sample supply source and with the last vessel of the series, with each of the other pumps being in operative association with adjacent pairs of the serially connected vessels, each pump having a suction side and a discharge side, a plurality of sample injection lines equal in number to the number of serially connected vessels, the first connecting the discharge side of the first pump with the diluent entry side of the last vessel, the others connecting the discharge side of a pump with the diluent entry side of a vessel upstream of the pairs of vessels associated with a pump, a plurality of sample withdrawal lines equal in number to the number of pumps, a first being connected to the suction side of the first pump, for supplying a sample of particulate solids containing fluid from the supply source, each of the other sample withdrawal lines connecting the diluent exit side of a downstream vessel of a pair of vessels in association with a pump, with the suction side of a pump, and a dilute sample outlet line located at the diluent exit side of the first vessel of the series for withdrawal of the diluted sample, whereby a sample of particulate solids containing fluid of relatively high solids concentration can be introduced into the suction side of the first pump of the series, as determined by the direction of flow of the sample of fluid specimen, and the diluted sample discharged from the diluent exit side of the first vessel of the series, as determined by the direction of flow of the diluent.

3. The apparatus of claim 2 wherein the vessels of the series are elongated, of tubular form and vertically oriented one with regard to the other, and each is packed to produce turbulent flow for efficient admixing of diluent and of the sample comprised of particulate solids.

4. The apparatus of claim 2 wherein the vessels of the series range in number from about 3 to about 5.

5. The apparatus of claim 2 wherein the pumps are of the gear type.

6. The apparatus of claim 2 wherein the pumps in operative association with adjacent pairs of the serially connected vessels are connected together by a common drive means.

7. The apparatus of claim 2 wherein the first pump of the series in operative association with a sample supply source and the last vessel of the series, and the other pumps in operative association with adjacent pairs of serially connected vessels are all connected together by a common drive means.

8. The apparatus of claim 7 wherein all of the pumps are of the gear type.

9. The apparatus of claim 2 wherein positive displacement pumps are employed.

* * * * *